United States Patent
Li et al.

(10) Patent No.: US 12,026,877 B2
(45) Date of Patent: Jul. 2, 2024

(54) DEVICE AND METHOD FOR PNEUMONIA DETECTION BASED ON DEEP LEARNING

(71) Applicant: Shenzhen Keya Medical Technology Corporation, Shenzhen (CN)

(72) Inventors: Jinchen Li, Beijing (CN); Guang Li, Beijing (CN); Chengwei Sun, Beijing (CN); Kunlin Cao, Kenmore, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 525 days.

(21) Appl. No.: 17/482,901

(22) Filed: Sep. 23, 2021

(65) Prior Publication Data

US 2022/0222812 A1 Jul. 14, 2022

(30) Foreign Application Priority Data

Jan. 14, 2021 (CN) .......................... 202110047682.1

(51) Int. Cl.
*G06T 7/00* (2017.01)
*G06F 18/2431* (2023.01)
*G06N 3/04* (2023.01)
*G16H 30/40* (2018.01)

(52) U.S. Cl.
CPC ........ *G06T 7/0012* (2013.01); *G06F 18/2431* (2023.01); *G06N 3/04* (2013.01);
(Continued)

(58) Field of Classification Search
CPC ......... G06T 7/0012; G06T 2207/10016; G06T 2207/10081; G06T 2207/20081;
(Continued)

(56) References Cited

U.S. PATENT DOCUMENTS

| 7,912,246 B1 | 3/2011 | Moon et al. |
| 11,076,824 B1 * | 8/2021 | Wang ..................... G06N 3/044 |

(Continued)

FOREIGN PATENT DOCUMENTS

| CN | 105678250 A | 6/2016 |
| CN | 106447625 A | 2/2017 |
| WO | 2018120942 A1 | 7/2018 |

OTHER PUBLICATIONS

Lee, Sue Han et al., Multi-Organ Plant Classification Based on Convolutional and Recurrent Neural Networks, Sep. 2018, IEEE Transaction on Image Processing, vol. 27 No. 9, pp. 4287-4301 (Year: 2018).*

(Continued)

*Primary Examiner* — Lewis G West
(74) *Attorney, Agent, or Firm* — BAYES PLLC

(57) ABSTRACT

The present disclosure provides a method, a device, and a non-transitory computer-readable storage medium for detecting a medical condition of an organ. The method includes obtaining 2D image sequences of the organ in a plurality of different directions and applying a plurality of classification branches to the 2D image sequences. Each classification branch receives a 2D image sequence of one direction and provides a classification result with respect to that direction. Each classification branch includes a convolutional neural network configured to extract first image features from the corresponding 2D image sequence and a recurrent neural network configured to extract second image features from the first image features. The method further includes fusing the classification results provided by the plurality of classification branches for detecting the medical condition.

20 Claims, 7 Drawing Sheets

(52) U.S. Cl.
CPC ... *G16H 30/40* (2018.01); *G06T 2207/10016* (2013.01); *G06T 2207/10081* (2013.01); *G06T 2207/20081* (2013.01); *G06T 2207/20084* (2013.01); *G06T 2207/30061* (2013.01)

(58) Field of Classification Search
CPC . G06T 2207/20084; G06T 2207/30061; G06T 2207/10076; G06T 7/0016; G06T 11/003; G06F 18/2431; G06F 18/24; G06F 18/253; G06N 3/04; G06N 3/044; G06N 3/045; G06N 3/08; G16H 30/40; G16H 50/20; G16H 50/70; G16H 30/20; Y02A 90/10; G06V 10/82; G06V 10/462
See application file for complete search history.

(56) References Cited

U.S. PATENT DOCUMENTS

| | | | | |
|---|---|---|---|---|
| 11,803,971 | B2* | 10/2023 | Hwang | G06V 10/762 |
| 11,816,185 | B1* | 11/2023 | Roth | G06V 10/7753 |
| 2018/0136633 | A1* | 5/2018 | Small | G06Q 30/018 |
| 2019/0122103 | A1 | 4/2019 | Gao et al. | |
| 2019/0365342 | A1* | 12/2019 | Ghaffarzadegan | A61B 7/04 |
| 2020/0258218 | A1* | 8/2020 | Xu | G06N 3/08 |
| 2020/0372641 | A1* | 11/2020 | Kim | G06V 10/764 |
| 2022/0036542 | A1* | 2/2022 | Sainz De Cea | G06T 7/0012 |
| 2023/0401364 | A1* | 12/2023 | Kothari | G06F 30/27 |
| 2024/0037911 | A1* | 2/2024 | Xin | G06V 10/806 |

OTHER PUBLICATIONS

Seeland, Marco et al., Multi-view classification with convolutional neural networks, Jan. 12, 2021, PLOS ONE, pp. 1-17 (Year: 2021).*
Office Action in related Chinese Application No. 202110047682.1 dated Aug. 19, 2022 (10 pages).

* cited by examiner

DEVICE AND METHOD FOR PNEUMONIA DETECTION BASED ON DEEP LEARNING

CROSS REFERENCE OF RELATED-APPLICATIONS

This application claims the benefit of priority to CN Application No. 2021100476821, filed on Jan. 14, 2021, the entire content of which is incorporated herein by reference.

TECHNICAL FIELD

The present disclosure relates to the technical field of medical image processing, and in particular, to an image classification device, method and non-transitory computer-readable storage medium for pneumonia detection using a deep learning network.

BACKGROUND

Some methods for automatically screening diseases such as pneumonia based on medical images are currently known.

Taking screening of pneumonia and COVID-19 as examples, some automatic screening methods include selecting n images from a sequence of 2D CT images and input them into a pre-trained first pneumonia deep learning model for classification, and the classification result labels whether each image is indicative of pneumonia. The images indicating pneumonia are then input into a pre-trained second deep learning model of COVID-19 for classification, and obtain a first classification result of whether the patient has COVID-19. The clinical diagnostic feature data corresponding to the images indicating pneumonia are input into the pre-trained SVM model for classification, and obtain a second classification result of whether the patient has COVID-19. The first classification result and the second classification result are merged to determine whether the patient has COVID-19. The disadvantages of this method include that (1) the number of CT images in the original sequence can vary significantly, and since only n images are selected from the CT sequence, certain original information of the pneumonia lesion will be lost; (2) the learning model has a series structure, and if the classification result obtained in the first step is not accurate, it will affect the subsequent determinations of COVID-19; and (3) the selected n images are directly input into the gated recurrent unit (GRU) time-series neural network. As a result, when n is large, usually cannot handle features efficiently, and when n is small, most of the information in the original image is not utilized, which seriously affects the diagnostic accuracy.

These automatic screening methods usually adopt a series model structure. For example, a deep learning detection model is used to detect the lung lesion area from the CT images first, and only the images of the detected lung lesion area are sent to a second stage network to perform diagnosis of a medical condition, such as COVID-19. There are errors in the detection of lung lesion area. Because images not part of the lung lesion areas will not be fed to the second stage network, any lesion area detection errors will seriously affect the determination of the second stage network. The second stage network only uses the middle layers of images where the lung lesion area are predicted, ignoring the information on the size and cross-layer difference of the lung lesion area, and there is serious information loss that affects the classification effect.

Although some automatic screening methods that use three-dimensional (3D) convolutional neural networks for pneumonia diagnosis have also been developed, such automatic screening models have various problems, such as high consumption of the video memory resource, time-consuming, heavy calculation load and low z-axis resolution (and the resulted problem of decreased accuracy). In addition, on the other hand, because the 3D convolutional neural network also performs down-sampling on the z-axis, when the lung lesion area is small, it is easy to lose lesion information, such as missing focus, which is not conducive to subsequent diagnosis.

SUMMARY

The present disclosure overcomes or at least alleviates the technical problems in the prior art described above.

In some embodiments, the present disclosure provides modeling methods and devices for automatically screening organ lesions based on CT images. In some embodiments, the disclosed methods and devices can learn features on three different sectional views with predetermined spatial relationships (for example, transverse, sagittal and coronal) by employing a model structure including three parallel two-dimensional (2D) structures, such that the features on the three sectional views can complement and supplement each other. Besides, the modeling methods and devices can utilize the LSTM network layer to model the relationship between layers, taking into account the size and the cross-layer information of lung lesion area, thus improving the screening precision compared to a 3D deep learning network. As explained in the BACKGROUND, the 3D deep learning nets network model performs poorly for small lesions due to the loss of information during down-sampling in the z-axis. Meanwhile, by structuring the model to include three parallel 2D networks, the embodiments of the present disclosure avoid several inherent problems of the 3D deep learning model, such as long training time, heavy calculation load, high consumption of calculation and video memory resource, among others.

According to a first aspect of the present disclosure, a method for detecting a medical condition of an organ is provided. The method includes obtaining 2D image sequences of the organ in a plurality of different directions and applying a plurality of classification branches to the 2D image sequences. Each classification branch receives a 2D image sequence of one direction and provides a classification result with respect to that direction. Each classification branch includes a convolutional neural network configured to extract first image features from the corresponding 2D image sequence and a recurrent neural network configured to extract second image features from the first image features. The method further includes fusing the classification results provided by the plurality of classification branches for detecting the medical condition.

According to another aspect of the present disclosure, there is provided an image classification device, including a storage device and a processor. The storage device is configured to store a learning network comprising a plurality of classification branches. The processor is configured to obtain 2D image sequences of the organ in a plurality of different directions and apply the plurality of classification branches to the 2D image sequences. Each classification branch receives a 2D image sequence of one direction and provides a classification result with respect to that direction. Each classification branch includes a convolutional neural network configured to extract first image features from the corresponding 2D image sequence and a recurrent neural network configured to extract second image features from the first image features. The processor further configured to fuse the classification results provided by the plurality of classification branches for detecting the medical condition.

According to another aspect of the present disclosure, there is provided a non-transitory computer-readable storage medium, with instructions store thereon. The instructions, when executed by a processor, may perform a method for detecting a medical condition of an organ. The method includes obtaining 2D image sequences of the organ in a plurality of different directions and applying a plurality of classification branches to the 2D image sequences. Each classification branch receives a 2D image sequence of one direction and provides a classification result with respect to that direction. Each classification branch includes a convolutional neural network configured to extract first image features from the corresponding 2D image sequence and a recurrent neural network configured to extract second image features from the first image features. The method further includes fusing the classification results provided by the plurality of classification branches for detecting the medical condition.

The disclosed devices and methods in the present disclosure may utilize a deep learning network that includes three parallel classification branches, each configured to process a 2D image sequence in one direction. The disclosed devices and methods achieve improved model performance, while reducing the demands for video memory and computing resources and increasing the computing speed.

In addition, because the recurrent neural network may fuse the feature information across different layers, the learning network may fuse not only the three-dimensional image features across images of different layers in each direction, but also the image features within the planes perpendicular to the three different directions. Extracting image features enables organ diagnosis and screening based on the three-dimensional spatial information of the organ area enables more accurate and precise diagnosis and prediction.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Such embodiments are demonstrative and not intended to be exhaustive or exclusive embodiments of the present method, device, or non-transitory computer readable medium having instructions thereon for implementing the method.

DETAILED DESCRIPTION

Figure 1:
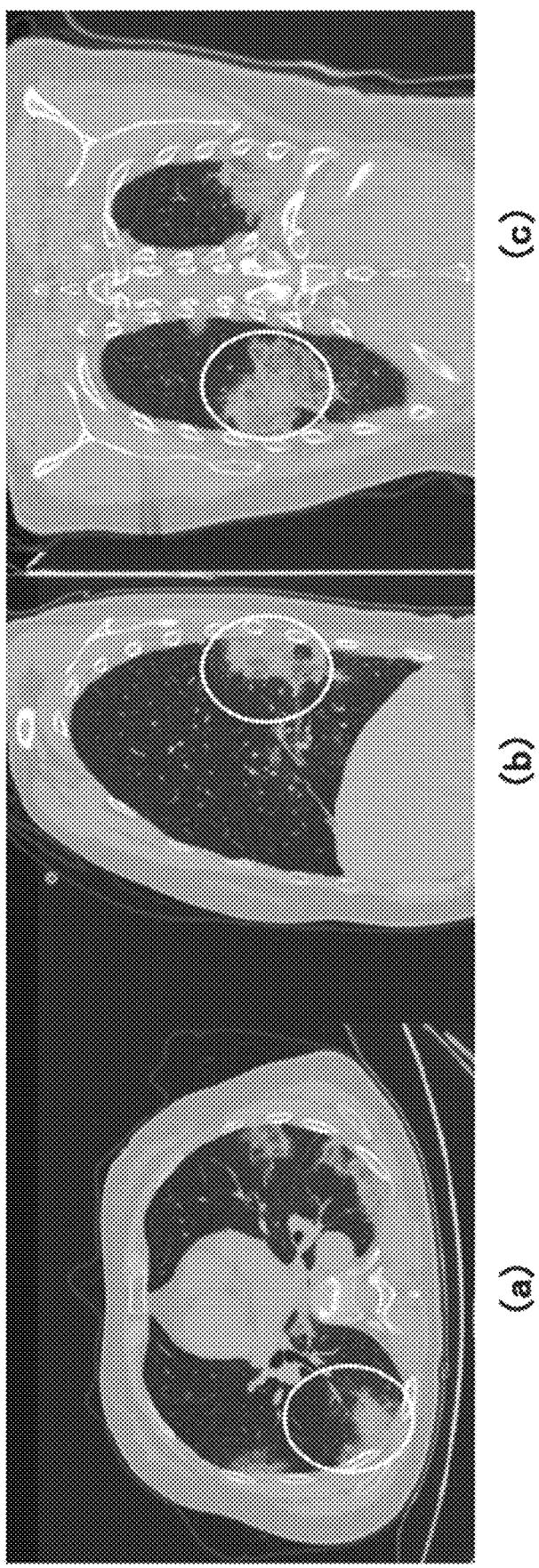
FIG. 1 shows transverse, sagittal and coronal images of a same patient.

For the purposes of explaining the concepts of the present disclosure, reference will now be made to the embodiments illustrated in the drawings and their corresponding descriptions. They are not intended to limit the scope of the disclosure. Alterations and further modifications to the described devices, systems, and methods, and any further application of the principles of the present disclosure are contemplated and included within the present disclosure as would normally occur to one skilled in the art to which the disclosure pertains. In particular, it is contemplated that the features, components, and/or steps described with respect to one embodiment may be combined with the features, components, and/or steps described with respect to other embodiments of the present disclosure. The order of steps of the method does not limit to the described or shown one. According to the disclosure, the order of steps may be switched according to actual requirements without departing from the spirit of the disclosure.

In the following descriptions, the lung is used as an example of an organ, pneumonia lesion information is used as an example of diagnosis and classification information of an organ and a CT image is used as an example of an acquired medical image, to illustrate various embodiments of the present disclosure, but the present disclosure is not limited thereto. The technical contents according to various embodiments of the present disclosure can also be applied to other organs, diagnosis and classification information of other types of lesions, and medical images of other modalities (such as but not limited to MRI, PET, etc.), although not explicitly described here.

In screening and diagnosis of pneumonia, multiple 2D CT images of the target site (for example, a lung) are usually acquired by an image acquisition device. The number of the acquired images is usually not a fixed number and is usually large. According to embodiments of the present disclosure, the acquired images (e.g., transverse images) may be resampled to obtain a fixed number of transverse images. Resampling the transverse images can reduce and fix the number of 2D images for further processing. Furthermore, considering that the size, location, and features of the target area of pneumonia are typically very different in the three directions, analyzing images of the three directions respectively may extract features related to the target area more comprehensively. Therefore, the disclosed embodiments also generate coronal images and sagittal images from the acquired 2D transverse images through image processing technology and analyze the transverse, coronal, and sagittal images separately for diagnosis purpose. Due to the thorough use of the image information contained in the acquired images, when the features in one direction are missing or lost during sampling, it may be compensated by the features extracted from the other two directions, thus reducing false positives and false negatives during the diagnosis of pneumonia.

FIG. 1 shows transverse, sagittal and coronal images of a target area of lung of the same patient. As shown in FIG. 1, (a) is a transverse image, (b) is a sagittal image, and (c) is a coronal image. The white circles marked in the three images indicate the same pneumonia lesion area that is presented in the three different views, i.e., transverse, sagittal and coronal sectional views. From the presentation of these images, it can be seen that the characteristics of the same lesion in the three views are different, corresponding to the 2D feature distribution of the 3D information in the images of three directions. Generally, a 2D transverse image can be acquired by a CT image acquisition device. As described above, in order to diagnose pneumonia, images of other two directions, such as sagittal images and coronal images, may be obtained to obtain three-dimensional spatial information of the target site to be diagnosed. To this end, image processing technology may be used to perform reconstruction and multi-planar reconstruction on the 2D transverse images to obtain the sagittal images and the coronal images. Then 2D image features can be extracted from images of the three directions including transverse, sagittal and coronal images to diagnose whether the patient has pneumonia. By generating sagittal and coronal images from the acquired 2D transverse images, the disclosed method does not require actually acquiring images of all three directions of the target area of the patient, which substantially reduces the patient's examination time and unnecessary radiation exposure.

Figure 2:
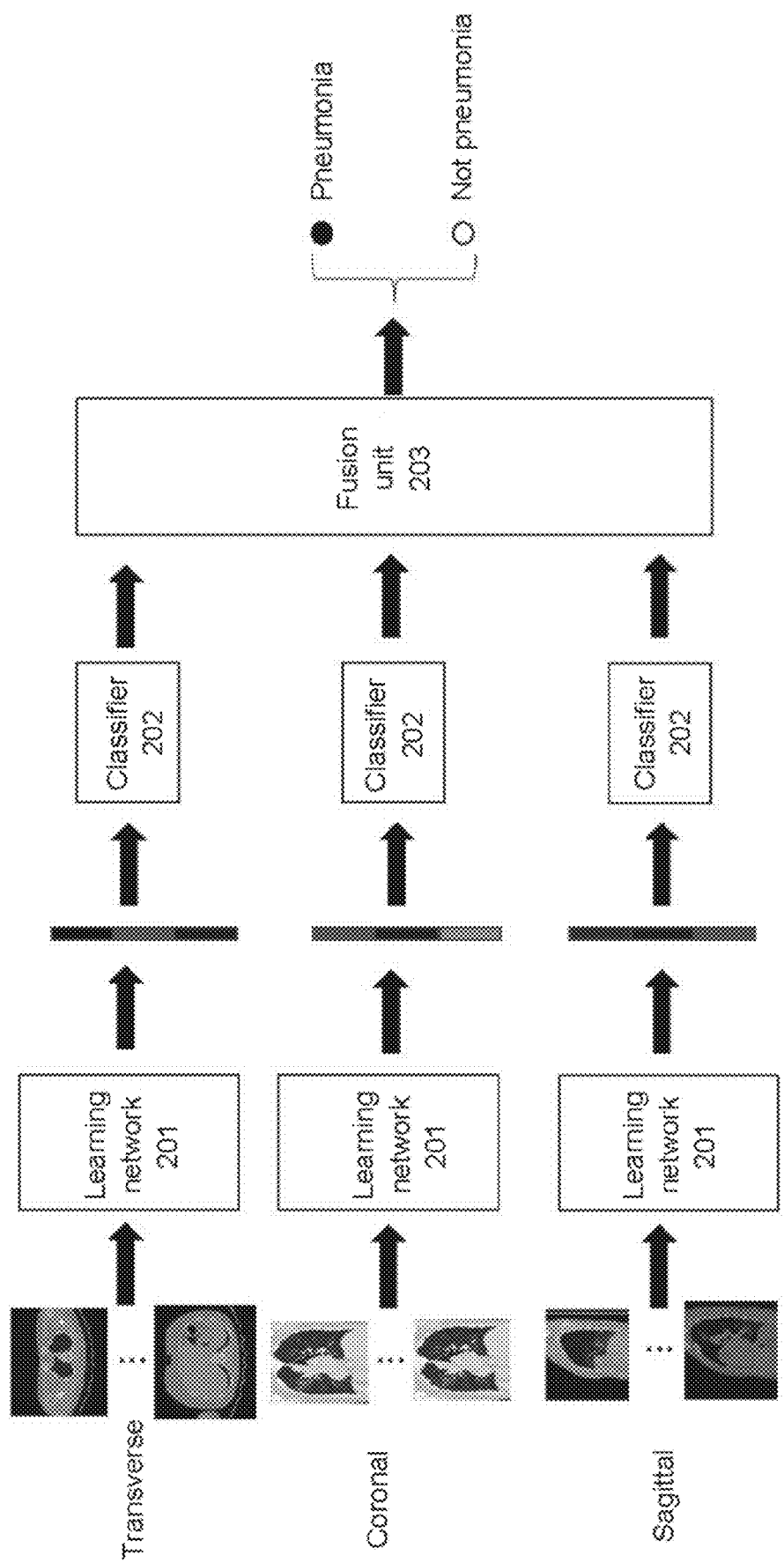
FIG. 2 shows an exemplary framework of an image classification model according to an embodiment of the present disclosure.

Three parallel classification branches may be constructed to analyze the 2D image features of the three sections including the transverse, sagittal and coronal sections, respectively. These three classification branches may be referred to as a first classification branch, a second classification branch and a third classification branch, respectively. As an example, FIG. 2 shows an exemplary framework of an image classification model according to an embodiment of the present disclosure. In some embodiments, the structure of each classification branch may be the same. For example, the architecture of the image classification model as shown in FIG. 2 may include three classification branches (each including individual learning network 201 and classifier 202) and a fusion unit 203 on the output side of the three classification branches. According to an embodiment of the present disclosure, each learning network 201 may include a convolutional neural network (CNN) (for example, resnet50, computer vision group (VGG), etc.) and a recurrent neural network (RNN) (for example, a Long Short-Term Memory (LSTM) network, Gated Recurrent Unit (GRU), etc.).

As shown in FIG. 2, the input may include three 2D image sequences of the site where the organ (for example, a lung) is located. The three 2D image sequences are stacks of images along three different directions, respectively. According to some embodiments, the first direction, the second direction, and the third direction may be orthogonal to each other. For example, for CT images, the first direction may be a direction perpendicular to a transverse plane, the second direction may be a direction perpendicular to a coronal plane, and the third direction may be a direction perpendicular to a sagittal orientation from an anatomical point of view. Accordingly, the 2D image sequence of the first direction may be transverse images acquired directly by CT or resampled transverse images, and the 2D image sequence of the second and third directions may be coronal and sagittal images generated based on the acquired transverse images. Hereinafter, the directions perpendicular to the transverse, coronal, and sagittal planes are respectively used as examples of the first, second, and third directions for the sake of description, but it should be noted that the present disclosure is not limited thereto. In some alternative embodiments, the three directions may deviate from the orthogonal directions, respectively, for an angle between 0 and 45 degrees.

After obtaining the 2D image sequences of the three directions, they may be fed into three parallel classification branches. The first classification branch is applied to the transverse images (therefore referred to as the "transverse branch"), the second classification branch is applied to the coronal images (therefore referred to as the "coronal branch"), and the third classification branch is applied to the sagittal images (therefore referred to as the "sagittal branch"). In an embodiment, the model structures of the three classification branches may be identical. Taking the model structure of the transverse branch as an example, the 2D image sequence of the transverse orientation is received as the input of the model, based on which, a convolutional neural network (for example, resnet50, VG-G, etc.) may be used to extract (a sequence of) first image features. Then, a recurrent neural network (for example, LSTM, GRU, etc.) may be used to extract a second image feature based on the first image features. Subsequently, the extracted second image feature (for example, an expanded feature map) may be fed to the corresponding classifier 202 to obtain the classification result of the transverse branch. In some embodiments, the classification result may include such as but not limited to pneumonia probability information, pneumonia classification score, etc. Similarly, classification results may be obtained from the coronal and sagittal branches, respectively.

Then, using the fusion unit 203, the classification results of the three respective classification branches may be fused to obtain the final prediction result. The fusion unit 203 may implement various fusion algorithms. According to some embodiments, the fusion unit 203 may use, for example, a probability fusion algorithm. In the case where the organ is a lung and the 2D image sequence is a 2D lung CT image sequence, the prediction result may be a diagnosis result of pneumonia, e.g., the probability of the lung has pneumonia. According to an exemplary probability fusion algorithm, the average probability of the three classification branches is calculated, and a threshold may be set to 0.5. When the average probability is equal to or greater than 0.5, it is determined that the prediction result is that the patient has pneumonia. When the average probability is less than 0.5, it is determined that the prediction result is that the patient does not have pneumonia. In another example, the fusion unit 203 may also use, for example, a voting fusion algorithm to vote the prediction results of the three classification branches, and the one with the most votes is determined as the final classification. It is noted that any fusion algorithm known in the art or appearing in the future can be adopted by the fusion unit 203 for fusion processing.

As described above, the 2D convolution operations applied on images may obtain feature maps in the different directions, which is equivalent to extracting 3D features in the different sectional planes in a 3D space. Moreover, RNN may fuse the feature maps in each direction across different layers, which is equivalent to extracting 3D features across images of different layers in the same direction. This accounts to using 2D convolution operation to obtain 3D spatial information, thereby improving the feature extraction of the lesion area and obtaining more accurate and precise prediction results. In comparison, because methods that use 3D convolutional neural network to obtain 3D features have to perform down-sampling in the z-axis, they are prone to loss of lesion information, such as missing the lesion entirely when the lesion area is small, which impairs subsequent diagnosis. According to the present disclosure, compared to 3D convolutional neural networks, the use of three parallel 2D learning networks may significantly improve the feature extraction on the z-axis, avoid the loss of potential lesion information, and significantly increase the detection accuracy in the z-axis, which facilitates the physician's subsequent diagnosis.

Figure 3:
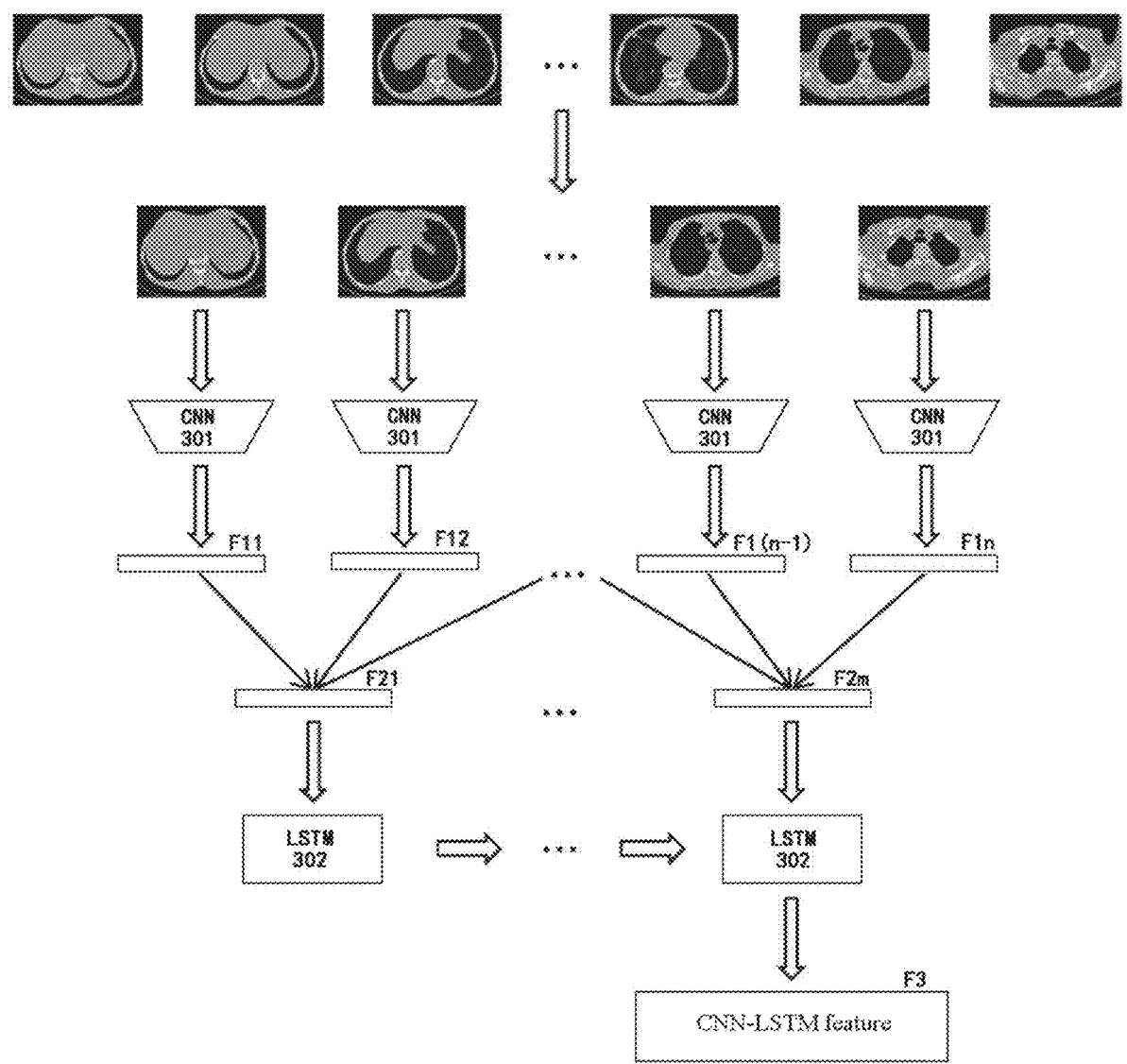
FIG. 3 shows an exemplary framework of a learning network in a single classification branch of an image classification model according to an embodiment of the present disclosure.

The architecture of the learning network in each classification branch of the image classification model according to an embodiment of the present disclosure will be described in detail below with reference to FIGS. 3 and 4. As shown in FIG. 3, the learning network in a single classification branch may include multiple CNN units 301 and multiple RNN (for example, LSTM) units 302. As described above, a fixed number of 2D transverse images may be obtained by resampling the acquired 2D transverse images. As an example, the number of the resampled 2D transverse images (e.g., n) in the resampled image sequence may be 120. Each of the n 2D transverse images in the image sequence is input to the corresponding CNN unit 301 for feature extraction. Image features F1*l* to F1*n* may be extracted from the respective 2D transverse images by n CNN units 301. In case that the image features F11 to F1*n* are not sufficiently distinguishable from each other, the features may also be collectively referred to as the first image features F1.

The RNN (for example, LSTM) unit 302 is prone to forgetting when extracting features from large-sized data, resulting in loss of global information. According to some embodiments, a plurality of image features F1*l* to F1*n* may be grouped into segments. In some embodiments, the segmentation may be performed unidirectionally along the sequence of the image features. For example, the image features may be segmented sequentially from front to back. According to some embodiments, each segment may include a certain number of image features, and the number may be in the range from about 10 to about 30, including but not limited to 10, 15, 20, 25, 30, and so on. These numbers are not intended to limit the present disclosure. Depending on the specific applications and various considerations, each segment may be composed of any appropriate number of image features. According to the embodiments of the present disclosure, image features may be segmented in a manner that some features overlap between segments. For example, according to some embodiments, the features in the overlapping part may account for one-third to one-half of the total features in a segment. It is contemplated that these overlapping ranges are not restrictive, but merely exemplary. Depending on the actual application and trade-off considerations (for example, the trade-off between model prediction accuracy and computational efficiency, etc.), any appropriate extent of overlapping features may be selected. As shown in FIG. 3, segmentation of image features F2*l* to F2*m* reduces the image features (if they are not distinguishable from each other, they can also be collectively referred to as intermediate image features F2), where m denotes the number of features after segmentation, which is also the number of LSTM units 302.

Figure 4:
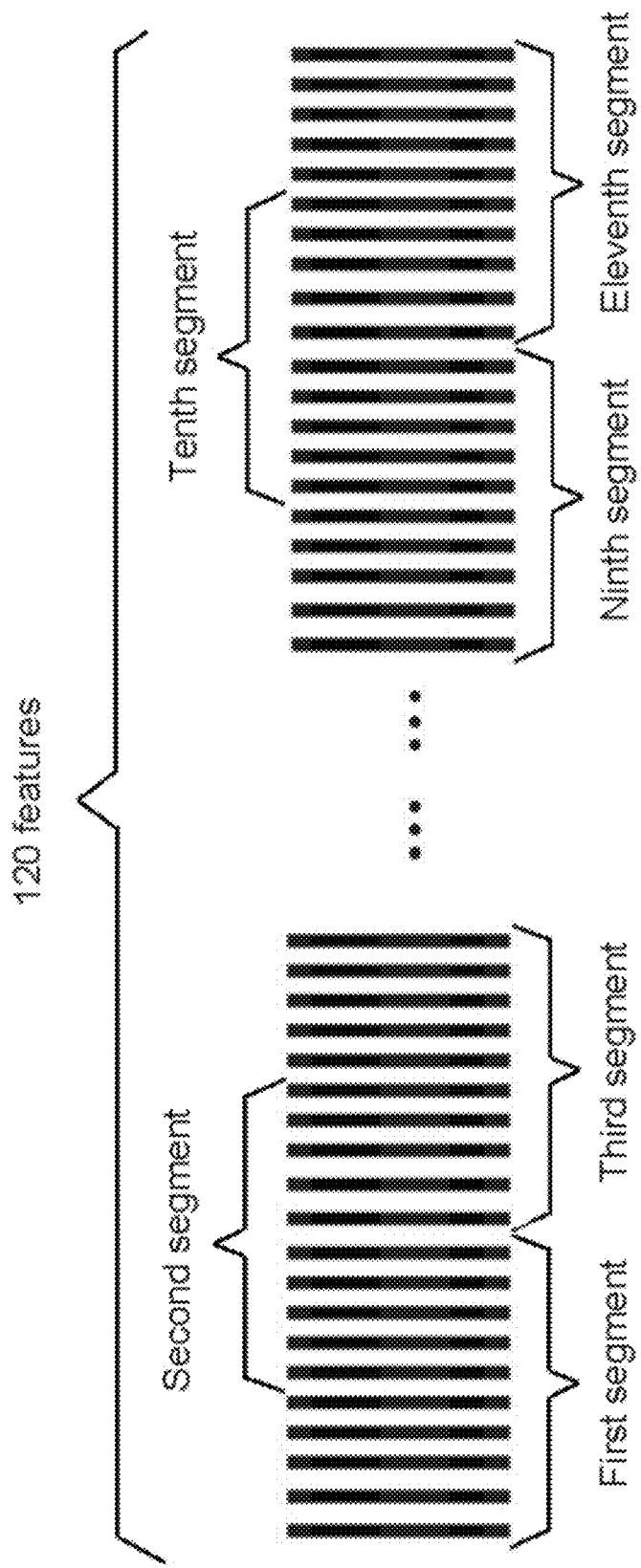
FIG. 4 illustrates segmentation of image features according to an embodiment of the present disclosure.

FIG. 4 illustrates the segmentation of image features according to one embodiment of the present disclosure. As shown in FIG. 4, a total of 120 features are obtained after convolution operation is performed using 120 CNN units 301. In some embodiments, in order to reduce the chance that the LSTM units 302 lose global information when processing a long sequence of features, these 120 features may be segmented. For example, 120 features may be segmented into 11 segments. According to an embodiment of the present disclosure, features may partially overlap between the first segment and the second segment. According to an example, as shown in 4, there are 10 features that overlap between the first segment and the second segment. According to another example, the number of overlapping features may be about 5 to 15, or any other appropriate number of overlapping features may be selected. By segmenting the image features sequentially from front to back as shown in FIG. 4, a total of 11 segments of image features including the first segment of features to the eleventh segment of features may be obtained as a result. According to some embodiments, the number of overlapping features between the segments may vary.

It is recognized that partial feature overlapping between segments may contribute to feature simplification and fusion before input to the LSTM unit 302, and a representative salient feature that best represents the multiple features of each segment may be input to the LSTM unit 302 for feature extraction, preventing the LSTM unit 302 from losing global information. On the other hand, partial feature overlap may avoid possible information omission or loss through feature redundancy within the segment.

Referring back to FIG. 3, after obtaining 11 segments of features, for example, 20 features in each segment of the 11 segments may be merged to obtain an intermediate image feature F2, which can be used as the salient feature of the segment. According to an embodiment of the present disclosure, the 20 features in each segment may be merge into one intermediate image feature F2 by taking a representative value (for example, but not limited to the mean value or the maximum value) of the 20 features in each segment. Subsequently, the 11 features obtained by taking the average value or the maximum value of the 11 sequential segments respectively are input into the corresponding LSTM units 302 for further feature extraction. Each LSTM unit 302 may output one intermediate image feature F2. In some embodiments, in order to incorporate the global feature of the image, only the feature output by the last LSTM unit 302 is adopted as the second image feature F3. The second image feature F3 is then input into the classifier 202 for final classification of pneumonia discrimination. Since the LSTM network may learn the information across different layers of the 2D CT image, the features of the pneumonia lesion area distributed across the layers are thus enhanced.

According to various embodiments of the present disclosure, since overall learning network model for imaging classification includes three parallel 2D networks that take 2D image sequences as inputs, several advantages may be achieved. On one hand, the training cost of the 2D network is low, the computational load is small, and the prediction time is shortened. On the other hand, the prediction accuracy (for example, image classification accuracy) may be better than that of a 3D network.

Figure 5:
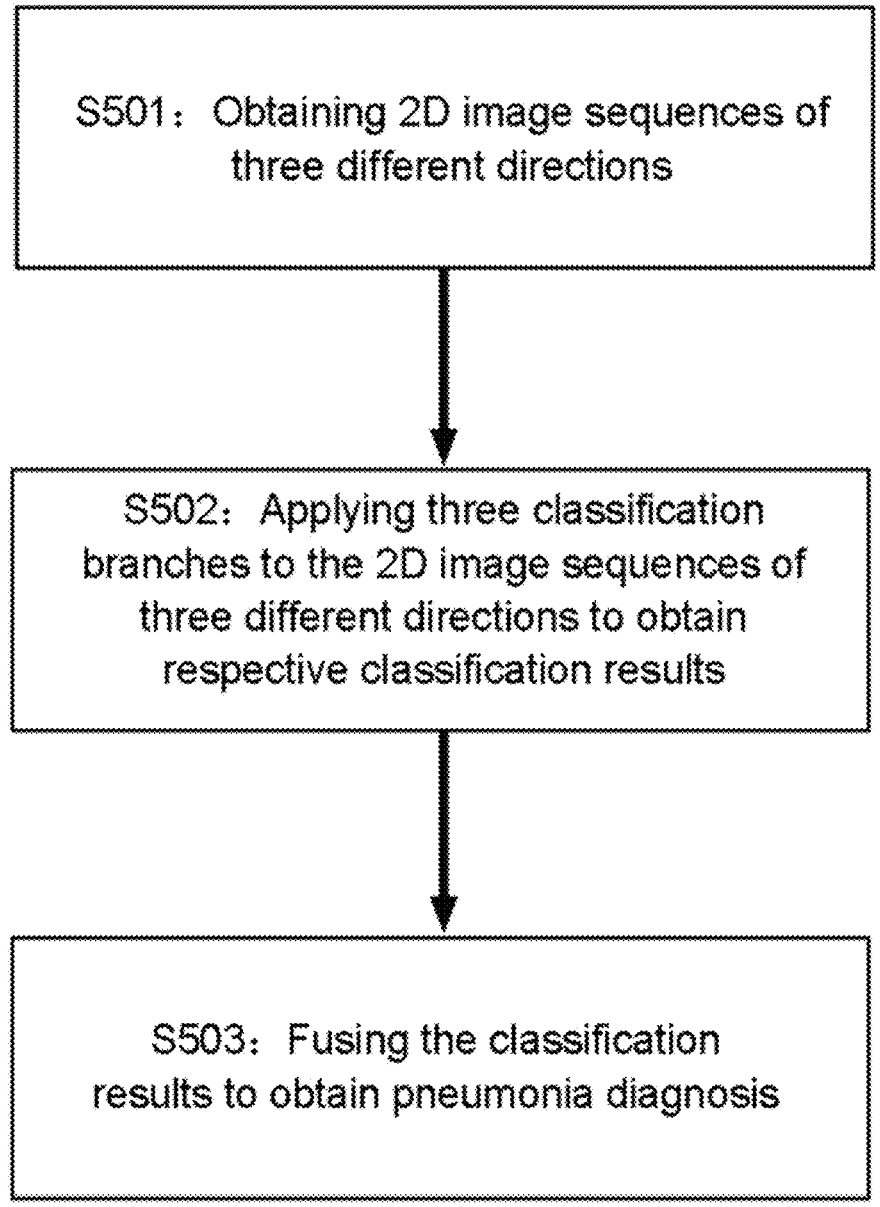
FIG. 5 shows a flowchart of a method for detecting pneumonia using an image classification model according to an embodiment of the present disclosure.

FIG. 5 shows a flowchart of a method for detecting pneumonia using an image classification model according to an embodiment of the present disclosure. In some embodiments, the image classification model used for the detection/diagnosis may be as shown in FIG. 3. In step S501, a 2D image sequence of a first direction, a 2D image sequence of a second direction, and a 2D image sequence of a third direction may be obtained. The image sequences may capture a site where the organ is located. According to some embodiments, the first direction, the second direction and the third direction are orthogonal or substantially orthogonal to each other. In some other embodiments, the first, second and third directions may deviate from the orthogonal directions for angle between 0 and 45 degrees. This deviation range is provided as an example only, not as a limitation on the scope of the present disclosure. According to an embodiment, the organ may include a lung. According to an embodiment of the present disclosure, the 2D image sequence of the first direction may be a sequence of transverse images of the lung, and the 2D image sequence of the second direction and the 2D image sequence of the third direction may be a coronal image sequence and a sagittal image sequence of the lungs respectively. In some embodiments, the transverse image sequence may be acquired by an image acquisition device, and the coronal and a sagittal image sequences may be obtained by image processing based on the transverse image sequence of the lung.

As shown in FIG. 5, the method may further include step S502, where the three image sequences are input into three parallel classification branches, respectively. For example, each classification branch may include multiple CNN units 301 configured to extract a sequence of first image features based on the input, and multiple RNN (e.g., LSTM) units 302 configured to extract a second image feature based on the first image features. And the extracted second image feature may be fed to a respective classifier 302, to obtain classification information of the classification branch. According to an embodiment of the present disclosure, before extracting the second image feature using LSTM units 302 based on the first image features, the first image features may be segmented and a representative value (e.g., a mean or a maximum value) of the image features in each segment may be used as input into each LSTM unit 302 of the LSTM network, as explained in detail above. In some embodiments, as described above, the first image features may be segmented in a manner that at least part of the image features overlap between the segments.

The method may further include step S503, where the second image features obtained by the LSTM units 302 are fused by a fusion unit 203. For example, a probability fusion algorithm may be implemented by the fusion unit 203 to fuse classification results of the classification branches. According to some embodiments, the image classification result may be, for example, a pneumonia diagnosis prediction result.

Figure 6:
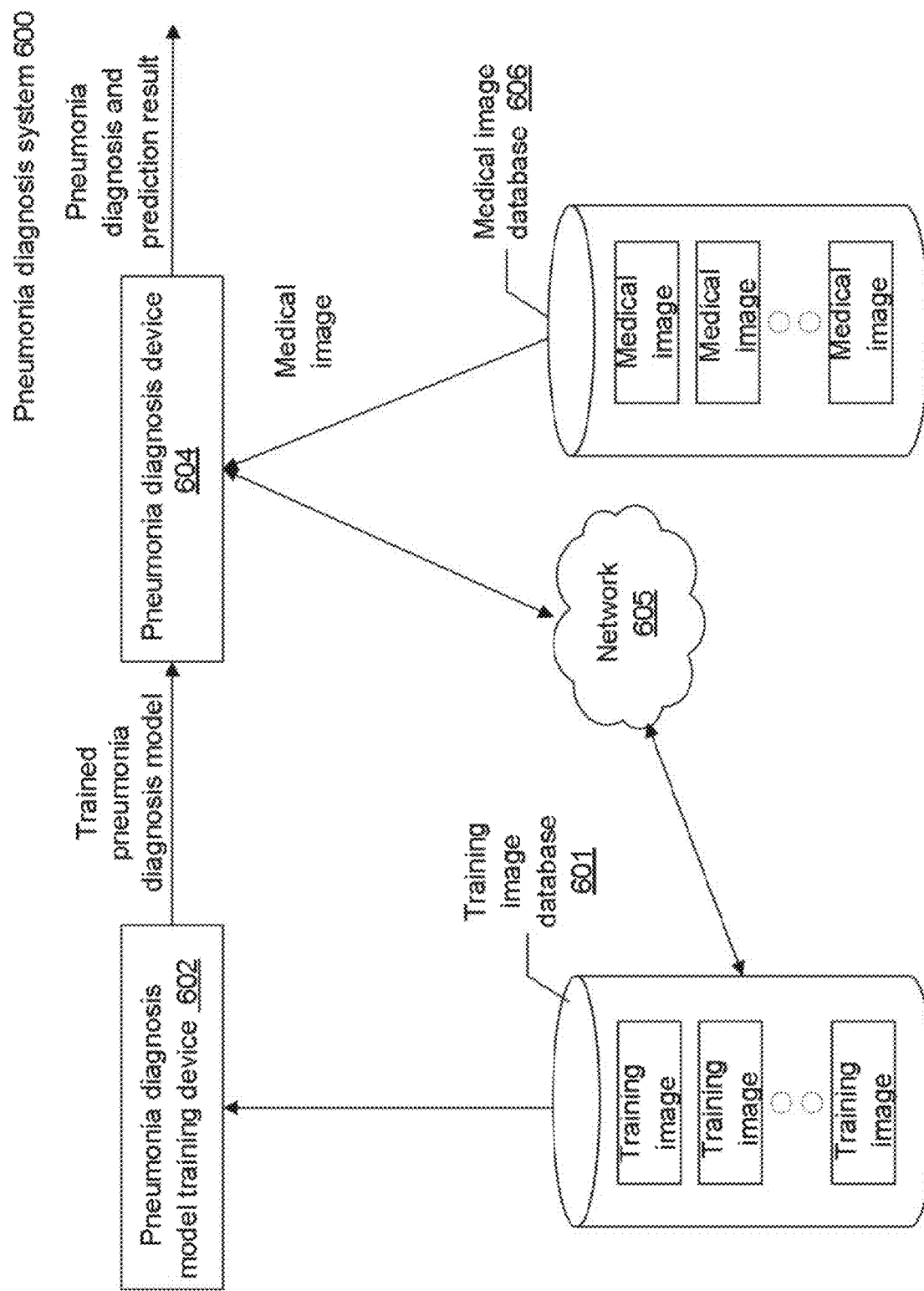
FIG. 6 shows a schematic diagram of an exemplary pneumonia diagnosis system according to an embodiment of the present disclosure.

FIG. 6 shows a schematic configuration diagram of an exemplary pneumonia diagnosis system according to an embodiment of the present disclosure.

The training phase and the prediction phase of pneumonia diagnosis modeling will be described in detail with reference to FIG. 6, which shows an outline of the implementation of the pneumonia diagnosis system 600. As shown, the system 600 may include a pneumonia diagnosis model training device 602 and a pneumonia diagnosis device 604. The pneumonia diagnosis model training device 602 obtains training images with ground truth from the training image database 601 to train the pneumonia diagnosis model, and as a result, outputs the trained pneumonia diagnosis model to the pneumonia diagnosis device 604. The pneumonia diagnosis device 604 is communicatively coupled to the medical image database 606. It applies the pneumonia diagnosis model to the medical images received from the medical image database 606 and outputs the result of the pneumonia prediction.

In some embodiments, the pneumonia diagnosis device 604 may be communicatively coupled to the training image database 601 via the network 605. The pneumonia prediction result obtained by the pneumonia diagnosis device 604, after being confirmed by a radiologist or clinician, may be fed back as a training sample to the training image database 601 for future use. In this manner, the training image database 601 may be augmented and expanded to help train models of improved accuracy and better prediction results.

Figure 7:
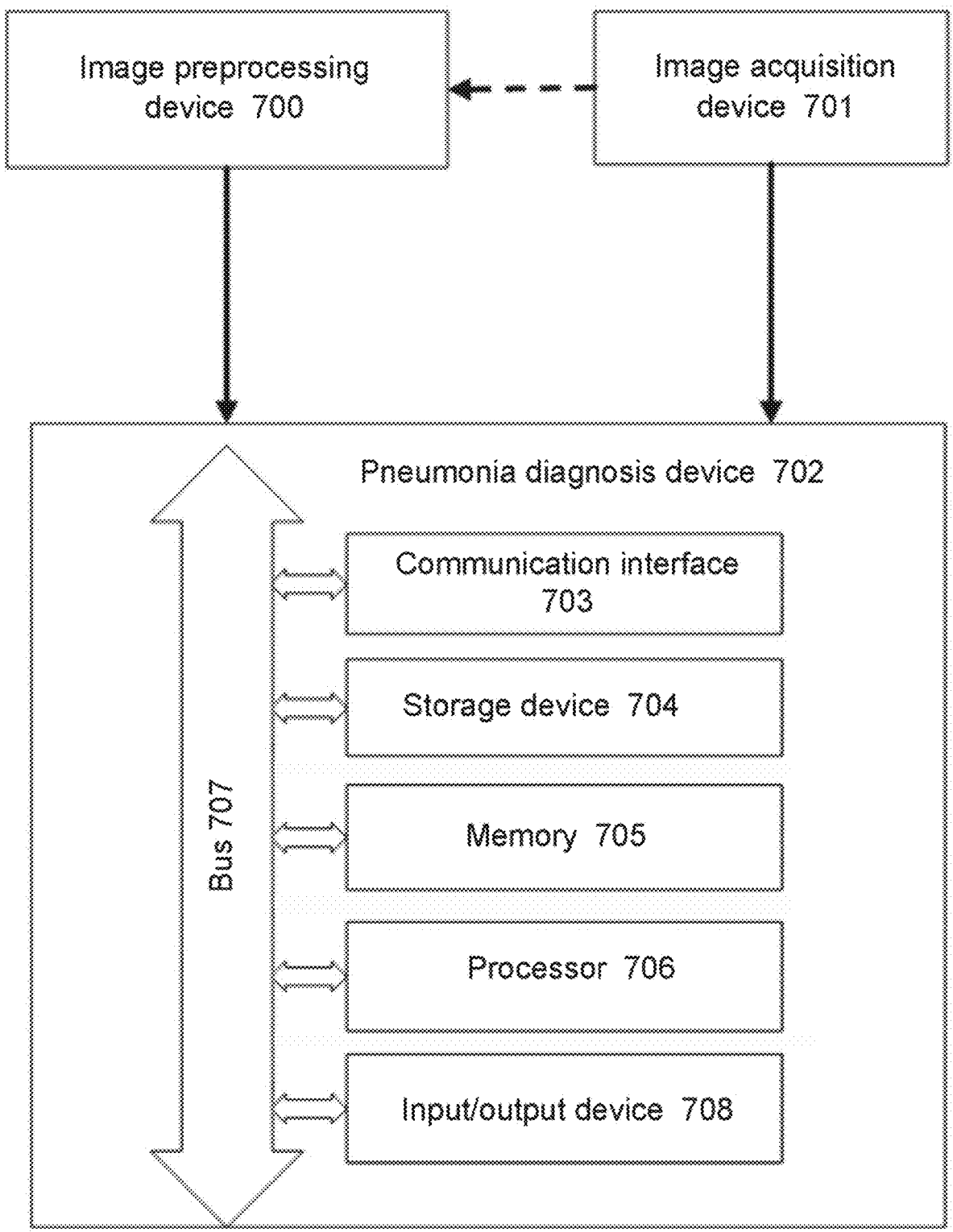
FIG. 7 shows a block diagram of an exemplary pneumonia diagnosis device according to an embodiment of the present disclosure.

A block diagram showing an exemplary pneumonia diagnosis system according to an embodiment of the present disclosure will be described with reference to FIG. 7. In some embodiments, the system may include, for example, an image preprocessing device 700, an image acquisition device 701, and a pneumonia diagnosis device 702. In some embodiments, the system may only include the pneumonia diagnostic device 702. According to an embodiment of the present disclosure, the pneumonia diagnosis device 702 may be, for example, an image classification device.

In some embodiments, the image acquisition device 701 may acquire and output images of any imaging modality, such as but not limited to CT, digital subtraction angiography (DSA), Magnetic Resonance Imaging (MRI), functional MRI, dynamic contrast enhanced diffusion URI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging, and the like.

In some embodiments, the image preprocessing device 700 may be communicatively connected to the image acquisition device 701 and the pneumonia diagnosis modeling device 702. According to one embodiment, the image preprocessing device 700 may directly or indirectly receive images from the image acquisition device 701, perform any image preprocessing operations on the image, including, for example, image resampling, and reconstructing the transverse images to obtain, for example, sagittal images and coronal images. In some embodiments, the image preprocessing device 700 may also be integrated with the pneumonia diagnosis device 702.

In some embodiments, the pneumonia diagnosis device 702 may be a dedicated computer or a general-purpose computer. The pneumonia diagnosis device 702 may be, for example, a hospital-customized computer for performing image acquisition and image processing tasks, for example, or a server in the cloud. As shown in FIG. 7, the pneumonia diagnosis device 702 may include a communication interface 703, a processor 706, a memory 705, a storage device 704, a bus 707, and input/output device 708. For example, the communication interface 703, the processor 706, the memory 705, the storage device 704 and the input/output device 708 may be connected and communicated with one another.

In some embodiments, the communication interface 703 may include a network adapter, a cable connector, a serial connector, a USB connector, a parallel connector, a high-speed data transmission adapter (such as optical fiber, USB 3.0, Thunderbolt or the like), a wireless network adapter (such as Wi-Fi adapter), telecommunication (3G, 4G/LTE, 5G, 6G and beyond). The pneumonia diagnosis device 702 may be connected to the mage preprocessing device 700, the image acquisition device 701, and other components. In some embodiments, the pneumonia diagnosis device 702 may receive the generated images (for example, a 2D image sequence obtained after resampling the original images) from the image preprocessing device 700 via the communication interface 703. Besides, the pneumonia diagnosis device 702 may receive medical images (for example, original CT images) directly from the image acquisition device 701, and then process (for example, resample) the received images to obtain processed images, which may be input to the CNN units 301 for feature extraction.

In some embodiments, the memory 705/storage device 704 may be non-transitory computer-readable medium or machine-readable medium, such as read only memory (ROM), random access memory (RAM), a phase change random-access memory (PRAM), a dynamic random-access memory (DRAM) such as synchronous DRAM (SDRAM) or Rambus DRAM, a static random-access memory (SRAM), an Electrically-Erasable Programmable Read-Only Memory(EEPROM), flash memory, compact disc read-only memory (CD-ROM), digital versatile disk (DVD), magnetic storage device, etc., on which information or instructions which can be accessed and executed by a computer are stored in any format. In some embodiments, the trained pneumonia diagnosis model-related data may be stored in the storage device 704.

In some embodiments, the memory 705 may store computer-executable instructions that, when executed by the processor 706, may execute an image classification method such as the one described above in connection with FIG. 5.

In some embodiments, the processor 706 may be a single-core or multi-core processing device that includes one or more general processing devices, such as a microprocessor, a central processing unit (CPU), a graphics processing unit (GPU), and the like. More specifically, the processor 706 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The processor 706 may also be one or more dedicated processing devices such as application specific integrated circuits (ASICs), field programmable gate arrays (FPGAs), digital signal processors (DSPs), system-on-chip (SoC), and the like.

According to an embodiment of the present disclosure, the processor 706 may apply three classification branches to 2D image sequences of three different directions, respectively. Each classification branch may produce an image classification result (e.g., a probability that the lung has pneumonia), and the image classification results are fused to yield the final prediction result. In some embodiments, the network structure of each of the above three classification branches may be identical, the network parameters of the convolutional neural network in each classification branch may be different, and the network parameters of the recurrent neural network in each classification branch may be different.

The input/output device 708 may be any input and output device such as keyboard, mouse, punter, display, scanner, touch panel, via which an operator may interface with the computer. In some embodiments, prediction result may be output from the input/output device 708 for presentation to a user such as clinician, patient, etc.

Although the descriptions are made for the application of diagnosing pneumonia in lungs, the concept of the present disclosure can also be adapted and applied to the diagnosis of other diseases or other subjects. For example, the disclosed methods and devices can be applied for diagnosis liver fibrosis and prediction of its degree, diagnosis and classification of hepatitis, overall classification of images, and so on.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in a non-transitory computer readable storage medium, and when executed, may cause a machine to perform the described functions or operations and include any mechanism for storing information in the form accessible by a machine (e.g., computing device, electronic system, etc.), such as recordable or non-recordable media.

Moreover, while illustrative embodiments have been described herein, the scope includes any and all embodiments having equivalent elements, modifications, omissions, combinations (e.g., combinations of aspects across various embodiments), adaptations or alterations based on the present disclosure. The elements in the claims are to be interpreted broadly based on the language employed in the claims and not limited to examples described in the present specification or during the prosecution of the application. Further, the steps of the disclosed methods can be modified in any manner, including by reordering steps or inserting or deleting steps. It is intended, therefore, that the descriptions be considered as examples only, with a true scope being indicated by the following claims and their equivalents.

What is claimed is:

1. A computer-implemented method for detecting a medical condition of an organ, comprising:
    obtaining 2D image sequences of the organ in a plurality of different directions;
    applying, by a processor, a plurality of classification branches to the 2D image sequences, wherein each classification branch receives a 2D image sequence of one direction and provides a classification result with respect to that direction, wherein each classification branch comprises a convolutional neural network configured to extract first image features from the corresponding 2D image sequence and a recurrent neural network configured to extract second image features from the first image features; and
    fusing the classification results provided by the plurality of classification branches for detecting the medical condition.

2. The computer-implemented method according to claim 1, wherein the organ comprises a lung, the 2D image sequences comprise CT images, and the medical condition is a pneumonia in the lung.

3. The computer-implemented method according to claim 1, wherein the plurality of directions are substantially orthogonal to each other.

4. The computer-implemented method according to claim 3, wherein the 2D image sequences in the plurality of directions comprise a transverse image sequence, a coronal image sequence and a sagittal image sequence of the organ, respectively.

5. The computer-implemented method according to claim 4, further comprising:
    receiving an original transverse image sequence acquired by an image acquisition device;
    obtaining the transverse image sequence by resampling the original transverse image sequence; and
    generating the coronal image sequence and the sagittal image sequence based on the transverse image sequence.

6. The computer-implemented method according to claim 1, wherein the recurrent neural network comprises an LSTM network comprising a plurality of LSTM units, and extracting the second image features from the first image features comprises:
    segmenting the first image features into a plurality of segments;

determining a representative value of image features in each segment; and applying the plurality of LSTM units of the LSTM network to the representative values of the segments to obtain the second image features.

7. The computer-implemented method according to claim 6, wherein the segments comprise a first segment and a second segment that overlap in at least one first image feature.

8. The computer-implemented method according to claim 1, wherein a network structure is the same among the classification branches, network parameters of the convolutional neural networks are different among the classification branches, and network parameters of the recurrent neural networks are different among the classification branches.

9. A device for detecting a medical condition of an organ, comprising:
a storage device configured to store a learning network comprising a plurality of classification branches; and
a processor configured to:
obtain 2D image sequences of the organ in a plurality of different directions;
apply the plurality of classification branches to the 2D image sequences, wherein each classification branch receives a 2D image sequence of one direction and provides a classification result with respect to that direction, wherein each classification branch comprises a convolutional neural network configured to extract first image features from the corresponding 2D image sequence and a recurrent neural network configured to extract second image features from the first image features; and
fusing the classification results provided by the plurality of classification branches for detecting the medical condition.

10. The device according to claim 9, wherein the organ comprises a lung, the 2D image sequences comprise CT images, and the medical condition is a pneumonia in the lung.

11. The device according to claim 9, wherein the 2D image sequences in the plurality of directions comprise a transverse image sequence, a coronal image sequence and a sagittal image sequence of the organ, respectively.

12. The device according to claim 11, further comprising:
an interface configured to receive an original transverse image sequence acquired by an image acquisition device,
wherein the processor is further configured to:
obtain the transverse image sequence by resampling the original transverse image sequence; and
generate the coronal image sequence and the sagittal image sequence based on the transverse image sequence.

13. The device according to claim 9, wherein the recurrent neural network comprises an LSTM network comprising a plurality of LSTM units, and to extract the second image features from the first image features, the processor is further configured to:
segment the first image features into a plurality of segments;
determine a representative value of image features in each segment; and
apply the plurality of LSTM units of the LSTM network to the representative values of the segments to obtain the second image features.

14. The device according to claim 13, wherein the segments comprise a first segment and a second segment that overlap in at least one first image feature.

15. The device according to claim 9, wherein a network structure is the same among the classification branches, network parameters of the convolutional neural networks are different among the classification branches, and network parameters of the recurrent neural networks are different among the classification branches.

16. A non-transitory computer-readable storage medium, which stores instructions that, when executed by a processor, perform a method for detecting a medical condition of an organ, the method comprising:
obtaining 2D image sequences of the organ in a plurality of different directions;
applying a plurality of classification branches to the 2D image sequences, wherein each classification branch receives a 2D image sequence of one direction and provides a classification result with respect to that direction, wherein each classification branch comprises a convolutional neural network configured to extract first image features from the corresponding 2D image sequence and a recurrent neural network configured to extract second image features from the first image features; and
fusing the classification results provided by the plurality of classification branches for detecting the medical condition.

17. The non-transitory computer-readable storage medium according to claim 16, wherein the organ comprises a lung, the 2D image sequences comprise CT images, and the medical condition is a pneumonia in the lung.

18. The non-transitory computer-readable storage medium according to claim 16, wherein the 2D image sequences in the plurality of directions comprise a transverse image sequence, a coronal image sequence and a sagittal image sequence of the organ, respectively,
wherein the method further comprises:
receiving an original transverse image sequence acquired by an image acquisition device;
obtaining the transverse image sequence by resampling the original transverse image sequence; and
generating the coronal image sequence and the sagittal image sequence based on the transverse image sequence.

19. The non-transitory computer-readable storage medium according to claim 16, wherein the recurrent neural network comprises an LSTM network comprising a plurality of LSTM units, and extracting the second image features from the first image features comprises:
segmenting the first image features into a plurality of segments;
determining a representative value of image features in each segment; and
applying the plurality of LSTM units of the LSTM network to the representative values of the segments to obtain the second image features.

20. The non-transitory computer-readable storage medium according to claim 19, wherein the segments comprise a first segment and a second segment that overlap in at least one first image feature.

* * * * *